US012319941B2

(12) United States Patent
Zhou et al.

(10) Patent No.: US 12,319,941 B2
(45) Date of Patent: Jun. 3, 2025

(54) THERMOPHILIC RECOMBINANT TYPE II PULLULANASE AND APPLICATION THEREOF

(71) Applicant: Jiangnan University, Wuxi (CN)

(72) Inventors: Zhemin Zhou, Wuxi (CN); Li Zhou, Wuxi (CN); Ting Xie, Wuxi (CN); Wenjing Cui, Wuxi (CN); Zhongmei Liu, Wuxi (CN); Bo Pang, Wuxi (CN)

(73) Assignee: Jiangnan University, Wuxi (CN)

( * ) Notice: Subject to any disclaimer, the term of this patent is extended or adjusted under 35 U.S.C. 154(b) by 458 days.

(21) Appl. No.: 17/482,614

(22) Filed: Sep. 23, 2021

(65) Prior Publication Data

US 2022/0002698 A1 Jan. 6, 2022

Related U.S. Application Data

(63) Continuation of application No. PCT/CN2019/088342, filed on May 24, 2019.

(30) Foreign Application Priority Data

Apr. 19, 2019 (CN) ......................... 201910318050.7

(51) Int. Cl.
*C12N 9/44* (2006.01)
*C12N 1/20* (2006.01)
*C12N 15/70* (2006.01)

(52) U.S. Cl.
CPC ........... *C12N 9/2457* (2013.01); *C12N 1/205* (2021.05); *C12N 15/70* (2013.01); *C12Y 302/01041* (2013.01)

(58) Field of Classification Search
CPC ...... C12N 9/2457; C12N 1/205; C12N 15/70; C12Y 302/01041; C12R 2001/01; C12R 2001/19; C12P 7/48; C12P 19/00; C12P 19/04; C12P 19/14; C12P 19/16
See application file for complete search history.

(56) References Cited

U.S. PATENT DOCUMENTS 8,703,465 B2 * 4/2014 Borchert ................ C12N 9/246 435/201
2013/0017571 A1 * 1/2013 Borchert ................. C12P 19/16 435/150

FOREIGN PATENT DOCUMENTS

CN 101974556 A 2/2011
CN 102226166 A * 10/2011
CN 106755015 A 5/2017
CN 109593700 A 4/2019

OTHER PUBLICATIONS

Novagen pET System Manual 11th Edition (63 pages total); Copyright 2011 EMD Chemicals Inc., an affiliate of Merck KGaA, Darmstadt, Germany; obtained on Dec. 21, 23 from: https://www.emdmillipore.com/US/en/product/pET-24a-DNA-Novagen, EMD_BIO-69749 (Year: 2011).*

Pang B, Zhou L, Cui W, Liu Z, Zhou S, Xu J, Zhou Z. A Hyperthermostable Type II Pullulanase from a Deep-Sea Microorganism Pyrococcus yayanosii CH1. J Agric Food Chem. Aug. 28, 2019;67(34):9611-9617. doi: 10.1021/acs.jafc.9b03376 (Year: 2019).*

Malakhov et al. "SUMO fusions and SUMO-specific protease for efficient expression and purification of proteins". J Struct Funct Genomics. 2004;5(1-2):75-86. doi: 10.1023/B:JSFG.0000029237.70316.52. (Year: 2004).*

Novagen pET System Manual 11th Edition (63 pages total); Copyright 2011 EMD Chemicals Inc., an affiliate of Merck KGaA, Darmstadt, Germany; obtained on Dec. 21, 2023 from: https://www.emdmillipore.com/US/en/product/pET-24a-DNA-Novagen,EMD_BIO-69749 (Year: 2011).*

Rüdiger, A. et al. "Isolation and characterization of a heat-stable pullulanase from the hyperthermophilic archaeon Pyrococcus woesei after cloning and expression of its gene in *Escherichia coli*." Applied and Environmental microbiology. Feb. 1995;61(2): 567-75 doi: 10.1128/aem.61.2.567-575.1995 (Year: 1995).*

Peroutka et al. "SUMO Fusion Technology for Enhanced Protein Expression and Purification in Prokaryotes and Eukaryotes". In: Heterologous Gene Expression in *E. coli*. Methods in Molecular Biology, vol. 705. Humana Press. 2011. Chapter 2, pp. 15-30. https://doi.org/10.1007/978-1-61737-967-3_2. (Year: 2011).*

Jun et al., "Complete genome sequence of the obligate piezophilic hyperthermophilic archaeon Pyrococcus yayanosii CH1". J Bacteriol. Aug. 2011;193(16):4297-8. doi: 10.1128/JB.05345-11 (Year: 2011).*

NCBI Reference Sequence: WP_013906427.1 Organism: Pyrococcus yayanosii CH1; Assembly: GCF_000215995.1. Accessed Dec. 22, 2023; https://www.ncbi.nlm.nih.gov/protein/WP_013906427.1; From the Reference genome: ASM21599v1, First published in 2011. (4 pages total). (Year: 2011).*

Duan, X. and Wu, J. Enhancing the secretion efficiency and thermostability of a Bacillus deramificans pullulanase mutant (D437H/D503Y) by N-terminal domain truncation. Appl Environ Microbiol. Mar. 2015;81(6):pp. 1926-1931. doi: 10.1128/AEM.03714-14 (Year: 2015).*

GenBank WP_013906427.1, GenBank DATABASE,Dec. 12, 2017.

(Continued)

*Primary Examiner* — Aaron J Kosar
*Assistant Examiner* — Andrew T Moehlman
(74) *Attorney, Agent, or Firm* — IPRO, PLLC

(57) ABSTRACT

The present disclosure discloses a thermophilic recombinant type II pullulanase and the application thereof, and belongs to the technical field of genetic engineering. The present disclosure obtains a thermophilic recombinant type II pullulanase by heterologously expressing type II pullulanase in *Escherichia coli*. Its optimum pH is 6.6, it has better pH tolerance under the conditions of pH 5.8-8.0, and its optimum temperature is 95° C. After incubating at 95° C. for 10 h, the remaining enzyme activity is greater than 50%. It can exhibit higher specific enzyme activity under strong reducing conditions. For example, adding DTT to the culture environment can increase the specific enzyme activity of Sumo-$Pul_{Py}$ by 237.2%. The present disclosure also provides the combined truncation mutant Δ28N+Δ791C of type II pullulanase Sumo-$Pul_{Py}$. The specific enzyme activity of the enzyme mutant is 32.18±0.92 U/mg, which is 5.99 times as high as that of the wild-type enzyme, thereby having important industrial application value and potential.

11 Claims, 9 Drawing Sheets

Specification includes a Sequence Listing.

(56) References Cited

OTHER PUBLICATIONS

Wei, Tao et. al. "Pronucleus expression and characterization of Thermotoga lettingae TMO pullulanase TMP in recombinant *Escheichia coli*", J. Chin. Institute of Food Science and Tech. vol. 16, No. 8, Aug. 2016.

X. Y. Wang, Y. Nie, X. Q. Mu, Y. Xu, and R. Xiao, Disorder prediction-based construct optimization improves activity and catalytic efficiency of Bacillus naganoensis pullulanase, Sci. Rep., (2016) 6: 24574.

Y. L. Jiao, S. J. Wang, M. S. Lv, J. L. Xu, Y. W. Fang, S. Liu, A GH57 Family Amylopullulanase from Deep-Sea Thermococcus siculi: Expression of the Gene and Characterization of the Recombinant Enzyme, Curr. Microbiol., (2011) 62:222 228.

M. Nisha and T. Satyanarayana, Characterization of recombinant amylopullulanase (gt-apu) and truncated amylopullulanase (gt-apuT) of the extreme thermophile Geobacillus thermoleovorans NP33 and their action in starch saccharification, Appl. Microbiol. Biotechnol., (2013) 97: 6279-6292.

M. Nisha and T. Satyanarayana, The role of N1 domain on the activity, stability, substrate specificity and raw starch binding of amylopullulanase of the extreme thermophile Geobacillus thermoleovorans, Appl. Microbiol. Biotechnol., (2015) 99: 5461-5473.

J. H. Kim, M. Sunako, H. Ono, Y. Murooka, E. Fukusaki, and M. Yamashita, Characterization of the C-terminal truncated form of amylopullulanase from Lactobacillus plantarum L137, J. Biosci. Bioeng., (2009) 107: 124-129.

H. Y. Lin, H.-H. Chuang, F. P. Lin Biochemical characterization of engineered amylopullulanase from Thermoanaerobacter ethanolicus 39E-implicating the non-necessity of its 100 C-terminal amino acid residues, Extremophiles, (2008) 12:641-650.

* cited by examiner

SEQUENCE LISTING

<160> NUMBER OF SEQ ID NOS: 4

<210> SEQ ID NO 1
<211> LENGTH: 1207
<212> TYPE: PRT
<213> ORGANISM: Artificial sequence
<220> FEATURE:
<223> OTHER INFORMATION: Protein translated from synthetic DNA

<400> SEQUENCE: 1

Met Gly His His His His His His Met Ser Asp Ser Glu Val Asn Gln
1 5 10 15

Glu Ala Lys Pro Glu Val Lys Pro Glu Val Lys Pro Glu Thr His Ile
20 25 30

Asn Leu Lys Val Ser Asp Gly Ser Ser Glu Ile Phe Phe Lys Ile Lys
35 40 45

Lys Thr Thr Pro Leu Arg Arg Leu Met Glu Ala Phe Ala Lys Arg Gln
50 55 60

Gly Lys Glu Met Asp Ser Leu Arg Phe Leu Tyr Asp Gly Ile Arg Ile
65 70 75 80

Gln Ala Asp Gln Thr Pro Glu Asp Leu Asp Met Glu Asp Asn Asp Ile
85 90 95

Ile Glu Ala His Arg Glu Gln Ile Gly Gly Gln Arg Gly Ser Arg Arg
100 105 110

Val Leu Ser Leu Phe Val Val Phe Val Val Leu Gly Ser Leu Leu Ala
115 120 125

Leu Gln Pro Glu Val Lys Ala Gly Glu Pro Lys Pro Leu Asn Val Ile
130 135 140

Ile Val Trp His Gln His Gln Pro Tyr Tyr Tyr Asp Pro Val Gln Gly
145 150 155 160

Ile Tyr Thr Arg Pro Trp Val Arg Leu His Ala Ala Asn Asn Tyr Trp
165 170 175

Lys Met Ala Tyr Tyr Leu Ser Lys Tyr Pro Asp Val His Ala Thr Ile
180 185 190

-continued

```
Asp Leu Ser Gly Ser Leu Ile Ala Gln Leu Ala Asp Tyr Met Asn Gly
        195                 200                 205

Ala Lys Asp Ile Tyr Gln Ile Ile Thr Glu Lys Ile Ala Lys Gly Glu
    210                 215                 220

Pro Leu Thr Val Glu Glu Lys Trp Leu Met Leu Gln Ala Pro Gly Gly
225                 230                 235                 240

Phe Phe Asp His Thr Ile Pro Trp Asn Gly Glu Pro Val Thr Asp Lys
                245                 250                 255

Asn Gly Asn Pro Ile Arg Asp Phe Trp Asn Arg Tyr Thr Glu Leu Lys
            260                 265                 270

Asn Lys Met Leu Gln Ala Lys Ala Lys Tyr Ala Asn Leu Pro Leu Glu
        275                 280                 285

Glu Gln Lys Val Ala Val Thr Asn Glu Phe Thr Glu Gln Asp Tyr Ile
    290                 295                 300

Asp Leu Ala Val Leu Phe Asn Leu Ala Trp Ile Asp Tyr Asn Tyr Ile
305                 310                 315                 320

Met Asn Thr Pro Glu Leu Lys Ala Leu Tyr Glu Lys Val Asp Glu Gly
                325                 330                 335

Gly Tyr Thr Arg Glu Asp Val Arg Thr Val Leu Lys His Gln Met Trp
            340                 345                 350

Leu Leu Asn His Thr Phe Glu Glu His Glu Lys Ile Asn Leu Leu Leu
        355                 360                 365

Gly Asn Gly Asn Val Glu Val Thr Val Val Pro Tyr Ala His Pro Ile
    370                 375                 380

Gly Pro Ile Leu Asn Asp Phe Gly Trp Glu Glu Asp Phe Asp Ala His
385                 390                 395                 400

Val Lys Lys Ala His Glu Leu Tyr Lys Lys Tyr Leu Gly Ala Gly Lys
                405                 410                 415

Val Thr Pro Lys Gly Gly Trp Ala Ala Glu Ser Ala Leu Asn Asp Lys
            420                 425                 430

Thr Leu Glu Ile Leu Ala Glu Asn Gly Trp Gln Trp Val Met Thr Asp
        435                 440                 445

Gln Leu Val Leu Gln Lys Leu Gly Ile Pro Tyr Thr Val Glu Asn Tyr
    450                 455                 460

Tyr Lys Pro Trp Val Ala Glu Phe Asn Gly Arg Lys Ile Tyr Leu Phe
465                 470                 475                 480

Pro Arg Asp His Ala Leu Ser Asp Arg Val Gly Phe Thr Tyr Ser Gly
                485                 490                 495

Met Asn Gln Tyr Gln Ala Val Glu Asp Phe Ile Asn Glu Leu Leu Arg
            500                 505                 510

Ile Gln Lys Gln Asn Tyr Asp Gly Ser Leu Val Tyr Val Ile Thr Leu
        515                 520                 525

Asp Gly Glu Asn Pro Trp Glu His Tyr Pro Tyr Asp Gly Lys Leu Phe
    530                 535                 540

Leu Glu Thr Leu Tyr Lys Arg Leu Thr Glu Leu Gln Arg Gln Gly Leu
545                 550                 555                 560

Ile Arg Thr Leu Thr Pro Ser Glu Tyr Ile Lys Leu Tyr Gly Asp Lys
                565                 570                 575

Ala Asn Lys Leu Thr Pro Gln Met Met Glu Arg Leu Asp Leu Thr Gly
            580                 585                 590

Asp Asn Val Glu Ala Leu Leu Lys Ala Gln Ser Leu Gly Glu Leu Tyr
        595                 600                 605

Asp Met Ile Gly Val Lys Glu Glu Met Gln Trp Pro Glu Ser Ser Trp
```

-continued

```
    610                 615                 620

Ile Asp Gly Thr Leu Ser Thr Trp Ile Gly Glu Pro Gln Glu Asn Tyr
625                 630                 635                 640

Gly Trp Tyr Trp Leu Tyr Leu Ala Arg Lys Ala Leu Met Ala Gln Lys
                645                 650                 655

Asp Lys Met Ser Gln Glu Asn Trp Glu Lys Ala Tyr Glu Tyr Leu Leu
            660                 665                 670

Arg Ala Glu Ala Ser Asp Trp Phe Trp Trp Tyr Gly Ser Asp Gln Ser
        675                 680                 685

Ser Gly Gln Asp Tyr Thr Phe Asp Arg Tyr Phe Lys Thr Tyr Leu Tyr
    690                 695                 700

Glu Ile Tyr Arg Leu Ala Gly Leu Glu Pro Pro Ser Tyr Leu Tyr Gly
705                 710                 715                 720

Asn Tyr Phe Pro Asp Gly Glu Pro Tyr Thr Ile Arg Ala Leu Glu Gly
                725                 730                 735

Leu Gly Glu Gly Gln Val Lys Glu Tyr Ser Ser Met Ser Pro Leu Ala
            740                 745                 750

Glu Gly Val Ser Val Tyr Phe Asp Gly Glu Gly Val His Phe Val Val
        755                 760                 765

Lys Gly Asn Leu Glu Lys Phe Glu Ile Ser Ile Tyr Glu Lys Gly Glu
    770                 775                 780

Arg Val Gly Asn Thr Phe Thr Leu Leu Gln Glu Arg Pro Gly Glu Leu
785                 790                 795                 800

Lys Tyr Ser Leu Phe Pro Phe Ser Arg Asp Ser Val Gly Leu Leu Ile
                805                 810                 815

Thr Lys His Val Val Tyr Arg Asp Gly Lys Ala Glu Ile Tyr Ala Ala
            820                 825                 830

Thr Asp Tyr Glu Asn Thr Glu Lys Val Gly Glu Ala Ser Val Lys Gln
        835                 840                 845

Val Asp Gly Gly Val Glu Ile Val Val Pro Phe Asp Tyr Ile Lys Thr
    850                 855                 860

Pro Glu Asp Phe Tyr Phe Ala Val Ser Thr Val Lys Asp Gly Glu Leu
865                 870                 875                 880

Glu Ile Ile Thr Thr Pro Ile Glu Leu Lys Leu Pro Met Glu Val Lys
                885                 890                 895

Gly Val Pro Ile Val Asp Val Val Asp Pro Glu Gly Asp Asp Tyr Gly
            900                 905                 910

Pro Gly Thr Tyr Thr Tyr Pro Thr Asp Pro Val Phe Val Pro His His
        915                 920                 925

Leu Asp Leu Leu Arg Phe Arg Ile Leu Glu Gln Thr Asp Ala Tyr Val
    930                 935                 940

Met Glu Phe Tyr Phe Lys Glu Leu Gly Gly Asn Val Trp Asn Ala Pro
945                 950                 955                 960

Asn Gly Phe Ser Leu Gln Ile Ile Glu Val Tyr Leu Asp Phe Arg Glu
                965                 970                 975

Gly Gly Asn Thr Ser Ala Ile Lys Met Phe Pro Asp Gly Pro Gly Ala
            980                 985                 990

Asn Val Asn Leu Asp Pro Glu His  Pro Trp Asp Leu Ala  Leu Arg Ile
        995                 1000                1005

Ala Gly  Trp Asp Tyr Gly Asn  Leu Ile Val Leu Pro  Asn Gly Thr
    1010                1015                1020

Val Tyr  Gln Gly Glu Leu Gln  Ile Ser Ala Asp Pro  Val Asn Asn
    1025                1030                1035
```

-continued

Lys Ile Ile Val Lys Val Pro Lys Lys Tyr Ile Gln Ile Asp Glu
1040 1045 1050

Asp Tyr Gly Leu Trp Gly Val Val Leu Val Gly Ser Gln Asp Gly
1055 1060 1065

Tyr Gly Pro Asp Lys Trp Arg Pro Val Ala Val Glu Ala Glu Gln
1070 1075 1080

Trp Arg Leu Gly Gly Ala Asp Gln Gln Ala Val Ile Asp Asn Leu
1085 1090 1095

Ala Pro Arg Val Val Asp Leu Leu Val Pro Glu Gly Phe Lys Pro
1100 1105 1110

Thr Gln Glu Glu Gln Leu Ser Ser Tyr Asp Leu Glu Lys Lys Ile
1115 1120 1125

Leu Ala Thr Val Leu Met Ile Pro Leu Ile Glu Gly Ser Gly Gly
1130 1135 1140

Glu Glu Pro Ala Glu Thr Pro Arg Glu Thr Ala Ile Pro Ala Glu
1145 1150 1155

Ser Pro Thr Thr Thr Glu Ala Pro Thr Glu Thr Gln Ser Thr Thr
1160 1165 1170

Thr Ser Gln Gly Pro Thr Glu Thr Gln Thr Gly Gly Gly Ile Cys
1175 1180 1185

Gly Pro Val Ala Leu Leu Gly Leu Val Met Thr Pro Leu Leu Leu
1190 1195 1200

Arg Arg Arg Arg
1205

<210> SEQ ID NO 2
<211> LENGTH: 3624
<212> TYPE: DNA
<213> ORGANISM: Artificial sequence
<220> FEATURE:
<223> OTHER INFORMATION: Synthetic DNA

<400> SEQUENCE: 2
atgggtcacc accaccacca ccacatgtcg gactcagaag tcaatcaaga agctaagcca 60
gaggtcaagc cagaagtcaa gcctgagact cacatcaatt taaaggtgtc cgatggatct 120
tcagagatct tcttcaagat caaaaagacc actcctttaa gaaggctgat ggaagcgttc 180
gctaaaagac agggtaagga aatggactcc ttaagattct tgtacgacgg tattagaatt 240
caagctgatc agacccctga agatttggac atggaggata acgatattat tgaggctcac 300
agagaacaga ttggtggcca acgcggatcc cgtcgtgttc tgagcctgtt tgttgttttt 360
gttgttctgg gtagcctgct ggcactgcag ccggaagtta aagcaggtga accgaaaccg 420
ctgaatgtta ttattgtttg gcatcagcat cagccgtatt attatgatcc ggttcagggt 480
atttataccc gtccgtgggt tcgtctgcat gcagcaaata attattggaa aatggcatat 540
tatctgagca aatatccgga tgttcatgca accattgatc tgagcggtag cctgattgca 600
cagctggcag attatatgaa tggtgcaaaa gatatttatc agatcatcac cgaaaaaatc 660
gcaaaaggtg aaccgctgac cgttgaagaa aaatggctga tgctgcaggc accgggtggt 720
ttttttgatc ataccattcc gtggaatggt gaaccggtta ccgataaaaa tggtaatccg 780
attcgtgatt tttggaatcg ttataccgaa ctgaaaaata aaatgctgca ggcaaaagca 840
aaatatgcaa atctgccgct ggaagaacag aaagttgcag ttaccaatga atttaccgaa 900
caggattata ttgacctggc agttctgttt aatctggcat ggattgatta taattacatc 960

-continued atgaacaccc cggaactgaa agcactgtat gaaaaagttg atgaaggtgg ttatacccgt 1020
gaagatgttc gtaccgttct gaaacatcag atgtggctgc tgaatcatac ctttgaagaa 1080
catgaaaaaa tcaacctgct gctgggtaat ggtaatgttg aagttaccgt tgttccgtat 1140
gcacatccga ttggtccgat tctgaatgat tttggttggg aagaagattt tgatgcacat 1200
gttaaaaaag cacatgaact gtataaaaaa tacctgggtg caggtaaagt taccccgaaa 1260
ggtggttggg cagcagaaag cgcactgaat gataaaaccc tggaaattct ggcagaaaat 1320
ggttggcagt gggttatgac cgatcagctg gttctgcaga aactgggtat tccgtatacc 1380
gttgaaaatt attataaacc gtgggttgca gaatttaatg gtcgtaaaat ttacctgttc 1440
ccgcgtgatc atgcactgag cgatcgtgtt ggttttacct atagcggtat gaatcagtat 1500
caggcagttg aagattttat taatgagctg ctgcgtattc agaaacagaa ttatgatggt 1560
agcctggttt atgttattac cctggatggt gaaaatccgt gggaacatta tccgtatgat 1620
ggtaaactgt ttctggaaac cctgtataaa cgtctgaccg aactgcagcg tcagggtctg 1680
attcgtaccc tgaccccgag cgaatatatt aaactgtatg gtgataaagc caacaaactg 1740
accccgcaga tgatggaacg tctggatctg accggtgata atgttgaagc actgctgaaa 1800
gcacagagcc tgggtgaact gtatgatatg attggtgtta aagaagaaat gcagtggccg 1860
gaaagcagct ggattgatgg tacactgagc acctggattg gtgaaccgca ggaaaattat 1920
ggttggtatt ggctgtatct ggcacgtaaa gcactgatgg cacagaaaga taaaatgagc 1980
caggaaaatt gggaaaaagc atacgaatat ctgctgcgtg cagaagcaag cgattggttt 2040
tggtggtatg gtagcgatca gagcagcggt caggattata cctttgatcg ttattttaaa 2100
acctacctgt acgaaattta ccgtctggca ggtctggaac cgccgagcta tctgtatggt 2160
aattattttc cggatggtga accgtatacc attcgtgcac tggaaggtct gggtgaaggt 2220
caggttaaag aatatagcag catgagcccg ctggcagaag gtgttagcgt ttattttgat 2280
ggtgaaggtg ttcattttgt tgttaaaggt aatctggaaa aattcgaaat cagcatttac 2340
gaaaaaggtg aacgtgttgg taataccttt accctgctgc aggaacgtcc gggtgaactg 2400
aaatatagcc tgtttccgtt tagccgtgat agcgttggtc tgctgattac caaacatgtt 2460
gtttatcgtg atggtaaagc agaaatttat gcagcaaccg attatgaaaa taccgaaaaa 2520
gttggtgaag caagcgttaa acaggttgat ggtggtgttg aaattgttgt tccgtttgat 2580
tatatcaaaa ccccggaaga tttttatttc gcagttagca ccgttaaaga tggtgaactg 2640
gaaattatta ccaccccgat tgaactgaaa ctgccgatgg aagttaaagg tgttccgatt 2700
gttgatgttg ttgatccgga aggtgatgat tatggtccgg gtacatatac ctatccgacc 2760
gatccggttt ttgttccgca tcatctggat ctgctgcgtt ttcgtattct ggaacagacc 2820
gatgcatacg ttatggaatt ttattttaaa gagctgggtg gtaatgtttg gaatgcaccg 2880
aatggtttta gcctgcagat tattgaagtt tatctggatt ttcgtgaggg tggtaatacc 2940
agcgcaatta aaatgtttcc ggatggtccg ggtgcaaatg ttaatctgga ccctgaacat 3000
ccgtgggatc tggcactgcg tattgcaggt tgggattatg gtaatctgat tgttctgccg 3060
aatggtacag tttatcaggg tgaactgcag attagcgcag atccggttaa taataaaatt 3120
attgtgaaag tgcctaaaaa atacatccag attgatgaag attacggtct gtggggtgtt 3180
gttctggttg gtagccagga tggttatggt ccggataaat ggcgtccggt tgcagttgaa 3240
gcagaacagt ggcgtctggg tggtgcagat cagcaggcag ttattgataa tctggcaccg 3300
cgtgttgttg atctgctggt tccggaaggt tttaaaccga cccaggaaga acagctgagc 3360
agctatgatc tggaaaaaaa aattctggca accgttctga tgattccgct gattgaaggt 3420
agcggtggtg aagaaccggc agaaaccccg cgtgaaaccg caattccggc agaaagcccg 3480
accaccaccg aagcaccgac cgaaacccag agcaccacca ccagccaggg tccgaccgaa 3540
acccagaccg gtggtggtat ttgtggtccg gttgcactgc tgggtctggt tatgaccccg 3600
ctgctgctgc gtcgtcgtcg ttaa 3624

<210> SEQ ID NO 3
<211> LENGTH: 872
<212> TYPE: PRT
<213> ORGANISM: Artificial sequence
<220> FEATURE:
<223> OTHER INFORMATION: Protein translated from synthetic DNA

<400> SEQUENCE: 3

Met Gly His His His His His His Met Ser Asp Ser Glu Val Asn Gln
1 5 10 15

Glu Ala Lys Pro Glu Val Lys Pro Glu Val Lys Pro Glu Thr His Ile
20 25 30

Asn Leu Lys Val Ser Asp Gly Ser Ser Glu Ile Phe Phe Lys Ile Lys
35 40 45

Lys Thr Thr Pro Leu Arg Arg Leu Met Glu Ala Phe Ala Lys Arg Gln
50 55 60

Gly Lys Glu Met Asp Ser Leu Arg Phe Leu Tyr Asp Gly Ile Arg Ile
65 70 75 80

Gln Ala Asp Gln Thr Pro Glu Asp Leu Asp Met Glu Asp Asn Asp Ile
85 90 95

Ile Glu Ala His Arg Glu Gln Ile Gly Gly Gln Arg Gly Ser Pro Lys
100 105 110

Pro Leu Asn Val Ile Ile Val Trp His Gln His Gln Pro Tyr Tyr Tyr
115 120 125

Asp Pro Val Gln Gly Ile Tyr Thr Arg Pro Trp Val Arg Leu His Ala
130 135 140

Ala Asn Asn Tyr Trp Lys Met Ala Tyr Tyr Leu Ser Lys Tyr Pro Asp
145 150 155 160

Val His Ala Thr Ile Asp Leu Ser Gly Ser Leu Ile Ala Gln Leu Ala
165 170 175

Asp Tyr Met Asn Gly Ala Lys Asp Ile Tyr Gln Ile Ile Thr Glu Lys
180 185 190

Ile Ala Lys Gly Glu Pro Leu Thr Val Glu Glu Lys Trp Leu Met Leu
195 200 205

Gln Ala Pro Gly Gly Phe Phe Asp His Thr Ile Pro Trp Asn Gly Glu
210 215 220

Pro Val Thr Asp Lys Asn Gly Asn Pro Ile Arg Asp Phe Trp Asn Arg
225 230 235 240

Tyr Thr Glu Leu Lys Asn Lys Met Leu Gln Ala Lys Ala Lys Tyr Ala
245 250 255

Asn Leu Pro Leu Glu Glu Gln Lys Val Ala Val Thr Asn Glu Phe Thr
260 265 270

Glu Gln Asp Tyr Ile Asp Leu Ala Val Leu Phe Asn Leu Ala Trp Ile
275 280 285

Asp Tyr Asn Tyr Ile Met Asn Thr Pro Glu Leu Lys Ala Leu Tyr Glu
290 295 300

Lys Val Asp Glu Gly Gly Tyr Thr Arg Glu Asp Val Arg Thr Val Leu

-continued

```
305                 310                 315                 320

Lys His Gln Met Trp Leu Leu Asn His Thr Phe Glu Glu His Glu Lys
                325                 330                 335

Ile Asn Leu Leu Leu Gly Asn Gly Asn Val Glu Val Thr Val Val Pro
            340                 345                 350

Tyr Ala His Pro Ile Gly Pro Ile Leu Asn Asp Phe Gly Trp Glu Glu
        355                 360                 365

Asp Phe Asp Ala His Val Lys Lys Ala His Glu Leu Tyr Lys Lys Tyr
    370                 375                 380

Leu Gly Ala Gly Lys Val Thr Pro Lys Gly Gly Trp Ala Ala Glu Ser
385                 390                 395                 400

Ala Leu Asn Asp Lys Thr Leu Glu Ile Leu Ala Glu Asn Gly Trp Gln
                405                 410                 415

Trp Val Met Thr Asp Gln Leu Val Leu Gln Lys Leu Gly Ile Pro Tyr
            420                 425                 430

Thr Val Glu Asn Tyr Tyr Lys Pro Trp Val Ala Glu Phe Asn Gly Arg
        435                 440                 445

Lys Ile Tyr Leu Phe Pro Arg Asp His Ala Leu Ser Asp Arg Val Gly
    450                 455                 460

Phe Thr Tyr Ser Gly Met Asn Gln Tyr Gln Ala Val Glu Asp Phe Ile
465                 470                 475                 480

Asn Glu Leu Leu Arg Ile Gln Lys Gln Asn Tyr Asp Gly Ser Leu Val
                485                 490                 495

Tyr Val Ile Thr Leu Asp Gly Glu Asn Pro Trp Glu His Tyr Pro Tyr
            500                 505                 510

Asp Gly Lys Leu Phe Leu Glu Thr Leu Tyr Lys Arg Leu Thr Glu Leu
        515                 520                 525

Gln Arg Gln Gly Leu Ile Arg Thr Leu Thr Pro Ser Glu Tyr Ile Lys
    530                 535                 540

Leu Tyr Gly Asp Lys Ala Asn Lys Leu Thr Pro Gln Met Met Glu Arg
545                 550                 555                 560

Leu Asp Leu Thr Gly Asp Asn Val Glu Ala Leu Leu Lys Ala Gln Ser
                565                 570                 575

Leu Gly Glu Leu Tyr Asp Met Ile Gly Val Lys Glu Glu Met Gln Trp
            580                 585                 590

Pro Glu Ser Ser Trp Ile Asp Gly Thr Leu Ser Thr Trp Ile Gly Glu
        595                 600                 605

Pro Gln Glu Asn Tyr Gly Trp Tyr Trp Leu Tyr Leu Ala Arg Lys Ala
    610                 615                 620

Leu Met Ala Gln Lys Asp Lys Met Ser Gln Glu Asn Trp Glu Lys Ala
625                 630                 635                 640

Tyr Glu Tyr Leu Leu Arg Ala Glu Ala Ser Asp Trp Phe Trp Trp Tyr
                645                 650                 655

Gly Ser Asp Gln Ser Ser Gly Gln Asp Tyr Thr Phe Asp Arg Tyr Phe
            660                 665                 670

Lys Thr Tyr Leu Tyr Glu Ile Tyr Arg Leu Ala Gly Leu Glu Pro Pro
        675                 680                 685

Ser Tyr Leu Tyr Gly Asn Tyr Phe Pro Asp Gly Glu Pro Tyr Thr Ile
    690                 695                 700

Arg Ala Leu Glu Gly Leu Gly Glu Gly Gln Val Lys Glu Tyr Ser Ser
705                 710                 715                 720

Met Ser Pro Leu Ala Glu Gly Val Ser Val Tyr Phe Asp Gly Glu Gly
                725                 730                 735
```

```
Val His Phe Val Val Lys Gly Asn Leu Glu Lys Phe Glu Ile Ser Ile
            740                 745                 750

Tyr Glu Lys Gly Glu Arg Val Gly Asn Thr Phe Thr Leu Leu Gln Glu
        755                 760                 765

Arg Pro Gly Glu Leu Lys Tyr Ser Leu Phe Pro Phe Ser Arg Asp Ser
    770                 775                 780

Val Gly Leu Leu Ile Thr Lys His Val Val Tyr Arg Asp Gly Lys Ala
785                 790                 795                 800

Glu Ile Tyr Ala Ala Thr Asp Tyr Glu Asn Thr Glu Lys Val Gly Glu
                805                 810                 815

Ala Ser Val Lys Gln Val Asp Gly Gly Val Glu Ile Val Val Pro Phe
            820                 825                 830

Asp Tyr Ile Lys Thr Pro Glu Asp Phe Tyr Phe Ala Val Ser Thr Val
        835                 840                 845

Lys Asp Gly Glu Leu Glu Ile Ile Thr Thr Pro Ile Glu Leu Lys Leu
    850                 855                 860

Pro Met Glu Val Lys Gly Val Pro
865                 870
```

<210> SEQ ID NO 4
<211> LENGTH: 2619
<212> TYPE: DNA
<213> ORGANISM: Artificial sequence
<220> FEATURE:
<223> OTHER INFORMATION: Synthetic DNA

<400> SEQUENCE: 4

```
atgggtcacc accaccacca ccacatgtcg gactcagaag tcaatcaaga agctaagcca     60

gaggtcaagc cagaagtcaa gcctgagact cacatcaatt taaaggtgtc cgatggatct    120

tcagagatct tcttcaagat caaaaagacc actcctttaa gaaggctgat ggaagcgttc    180

gctaaaagac agggtaagga aatggactcc ttaagattct tgtacgacgg tattagaatt    240

caagctgatc agacccctga agatttggac atggaggata acgatattat tgaggctcac    300

agagaacaga ttggtggcca acgcggatcc ccgaaaccgc tgaatgttat tattgtttgg    360

catcagcatc agccgtatta ttatgatccg gttcagggta tttatacccg tccgtgggtt    420

cgtctgcatg cagcaaataa ttattggaaa atggcatatt atctgagcaa atatccggat    480

gttcatgcaa ccattgatct gagcggtagc ctgattgcac agctggcaga ttatatgaat    540

ggtgcaaaag atatttatca gatcatcacc gaaaaaatcg caaaaggtga accgctgacc    600

gttgaagaaa aatggctgat gctgcaggca ccgggtggtt tttttgatca taccattccg    660

tggaatggtg aaccggttac cgataaaaat ggtaatccga ttcgtgattt ttggaatcgt    720

tataccgaac tgaaaaataa aatgctgcag gcaaaagcaa aatatgcaaa tctgccgctg    780

gaagaacaga aagttgcagt taccaatgaa tttaccgaac aggattatat tgacctggca    840

gttctgttta atctggcatg gattgattat aattacatca tgaacacccc ggaactgaaa    900

gcactgtatg aaaaagttga tgaaggtggt tatacccgtg aagatgttcg taccgttctg    960

aaacatcaga tgtggctgct gaatcatacc tttgaagaac atgaaaaaat caacctgctg   1020

ctgggtaatg gtaatgttga agttaccgtt gttccgtatg cacatccgat tggtccgatt   1080

ctgaatgatt ttggttggga agaagatttt gatgcacatg ttaaaaaagc acatgaactg   1140

tataaaaaat acctgggtgc aggtaaagtt accccgaaag gtggttgggc agcagaaagc   1200

gcactgaatg ataaaaccct ggaaattctg gcagaaaatg gttggcagtg ggttatgacc   1260
```

-continued

```
gatcagctgg ttctgcagaa actgggtatt ccgtataccg ttgaaaatta ttataaaccg   1320

tgggttgcag aatttaatgg tcgtaaaatt tacctgttcc cgcgtgatca tgcactgagc   1380

gatcgtgttg gttttaccta tagcggtatg aatcagtatc aggcagttga agattttatt   1440

aatgagctgc tgcgtattca gaaacagaat tatgatggta gcctggttta tgttattacc   1500

ctggatggtg aaaatccgtg ggaacattat ccgtatgatg gtaaactgtt tctggaaacc   1560

ctgtataaac gtctgaccga actgcagcgt cagggtctga ttcgtaccct gacccccgagc   1620

gaatatatta aactgtatgg tgataaagcc aacaaactga ccccgcagat gatggaacgt   1680

ctggatctga ccggtgataa tgttgaagca ctgctgaaag cacagagcct gggtgaactg   1740

tatgatatga ttggtgttaa agaagaaatg cagtggccgg aaagcagctg gattgatggt   1800

acactgagca cctggattgg tgaaccgcag gaaaattatg gttggtattg gctgtatctg   1860

gcacgtaaag cactgatggc acagaaagat aaaatgagcc aggaaaattg ggaaaaagca   1920

tacgaatatc tgctgcgtgc agaagcaagc gattggtttt ggtggtatgg tagcgatcag   1980

agcagcggtc aggattatac ctttgatcgt tattttaaaa cctacctgta cgaaatttac   2040

cgtctggcag gtctggaacc gccgagctat ctgtatggta attattttcc ggatggtgaa   2100

ccgtatacca ttcgtgcact ggaaggtctg ggtgaaggtc aggttaaaga atatagcagc   2160

atgagcccgc tggcagaagg tgttagcgtt tattttgatg gtgaaggtgt tcattttgtt   2220

gttaaaggta atctggaaaa attcgaaatc agcatttacg aaaaaggtga acgtgttggt   2280

aataccttta ccctgctgca ggaacgtccg ggtgaactga aatatagcct gtttccgttt   2340

agccgtgata gcgttggtct gctgattacc aaacatgttg tttatcgtga tggtaaagca   2400

gaaatttatg cagcaaccga ttatgaaaat accgaaaaag ttggtgaagc aagcgttaaa   2460

caggttgatg gtggtgttga aattgttgtt ccgtttgatt atatcaaaac cccggaagat   2520

ttttatttcg cagttagcac cgttaaagat ggtgaactgg aaattattac caccccgatt   2580

gaactgaaac tgccgatgga agttaaaggt gttccgtaa                          2619
```

THERMOPHILIC RECOMBINANT TYPE II PULLULANASE AND APPLICATION THEREOF

TECHNICAL FIELD

The disclosure relates to a thermophilic recombinant type II pullulanase and its application, belonging to the technical field of genetic engineering.

BACKGROUND

Pullulanase (EC 3.2.1.41) is a starch debranching enzyme that can hydrolyze α-1,6-glycosidic linkage in amylopectin, pullulan, and the α-limit dextrin and β-limit dextrin. According to the hydrolysis mode and product specificity, pullulanase can be divided into type I pullulanase and type II pullulanase. Type I pullulanase specifically hydrolyzes α-1,6-glycosidic linkages in pullulan and starch to produce maltotriose and linear oligosaccharides; type II pullulanase is a bifunctional enzyme that can not only hydrolyze α-1,6-glycosidic linkages in pullulan and amylopectin, having the function of type I pullulanase, but also hydrolyze α-1,4-glucosidic linkages in starch and related oligosaccharides by means of random endonucleation, having the function of α-amylase. Pullulanase has important applications in syrup production, citric acid fermentation, industrial brewing, and preparation of resistant starch and branched cyclodextrin.

In industry, the amylase process is generally divided two steps. First, α-amylase and starch are mixed under the condition of 95-105° C. and about pH 6.0 for liquefaction, and then glucoamylase is added under the condition of 60-65° C. and pH 4.0-4.5 for saccharification reaction. Thermophilic type II pullulanase naturally has excellent enzymatic properties, and its combination with α-amylase in the starch liquefaction step can not only improve the starch liquefaction efficiency, but also reduce the burden of the subsequent saccharification reaction and significantly shorten the reaction period.

The reaction conditions of the liquefaction and saccharification steps in the traditional amylase process are different, and the adjustment of the reaction parameters in the step conversion will have many negative effects on the entire processing procedure. For example, the overall reaction time is too long; changes in pH will result in the production of numerous salt ions; some excess by-products, such as panose, isopanose, and isomaltose, are often produced during the reaction.

A novel type II pullulanase with high catalytic efficiency and heat resistance can be screened to significantly improve the hydrolysis efficiency of amylase and reduce the cost of syrup production. More importantly, if the novel type II pullulanase has good thermal stability at high temperatures, then the enzymolysis process can always be maintained at high temperatures, which can significantly increase the concentration of syrup products and reduce the chance of bacteria infection and overall operating time. However, the currently reported type II pullulanase generally has low catalytic efficiency and poor thermal stability. For example, the catalytic efficiency of type II pullulanase derived from *Thermococcus siculi* HJ21 is 11.3 U/mg, and the half-life of type II pullulanase derived from *Thermococcus hydrothermalis* at 95° C. is only 10 min. Therefore, providing a thermophilic recombinant type II pullulanase with high enzyme activity has important application value for industrial starch processing.

SUMMARY

The present disclosure provides a recombinant *Escherichia coli* that (1) expresses type II pullulanase encoded by SEQ ID NO:3; or (2) expresses type II pullulanase encoded by SEQ ID NO:1. The *E. coli* has an enhanced protein secretion capacity in a culture environment containing strong reductants.

In one embodiment of the present disclosure, the strong reductants include $Fe^{2+}$, $Co^{2+}$, DTT and/or β-mercaptoethanol.

In one embodiment of the present disclosure, the pET series vector is used as the expression vector.

In one embodiment of the present disclosure, the nucleotide sequence encoding the type II pullulanase described in (1) is set forth in SEQ ID NO:4.

In one embodiment of the present disclosure, the nucleotide sequence encoding the type II pullulanase described in (2) is set forth in SEQ ID NO:2.

In one embodiment of the present disclosure, *E. coli* BL21 (DE3) is used as the host.

The present disclosure also provides a method for constructing any of the aforementioned recombinant *E. coli*, where the nucleotide sequence of the gene encoding type II pullulanase is synthesized, the synthesized nucleotide sequence is connected to the expression vector pET-24a (+) to obtain a recombinant plasmid, the tag sequence Sumo is connected to the recombinant plasmid to replace the T7 tag in the recombinant plasmid, and then the recombinant plasmid with replaced tag sequence is transformed into *E. coli* competent cells.

The present disclosure also provides a method for producing type II pullulanase, which uses the above-mentioned recombinant *E. coli* for fermentation.

In one embodiment of the present disclosure, the recombinant *E. coli* is inoculated into LB medium and cultured at 35-38° C. for 10-14 h, the cultured bacterial solution is inoculated into LB medium with an inoculum of 1%-5% and cultured with shaking at 35-38° C. until $OD_{600}$ reaches 0.4-0.6, and an inducer IPTG is added with a final concentration of 1-2 mmol/L and cultured with shaking at 200-220 rpm at 15-16° C. for 15-20 h.

The present disclosure also provides the application of the above-mentioned recombinant *Bacillus subtilis* in syrup production, citric acid fermentation, industrial brewing, preparation of resistant starch or preparation of branched cyclodextrin.

Beneficial Effects of the Present Disclosure

The present disclosure prepares a thermophilic recombinant type II pullulanase Sumo-$Pul_{Py}$ by expressing heterologous type II pullulanase in *E. coli*, which has the following characteristics:

1. the optimum pH is 6.6, with a better pH tolerance at pH 5.8-8.0;
2. the optimum temperature is 95° C., and the remaining enzyme activity is greater than 50% after heat preservation at 95° C. for 10 h;
3. it exhibits a higher specific enzyme activity under strong reducing conditions; Fe2+, Co2+, DTT, and β-mercaptoethanol can increase the specific enzyme activity of Sumo-$Pul_{Py}$ by more than 40%; the addition of DTT increases the specific enzyme activity of Sumo-$Pul_{Py}$ by 237.2%.

The present disclosure also provides a combined truncation mutant Δ28N+Δ791C obtained by truncating amino acids based on type II pullulanase Sumo-Pul$_{Py}$. The combined truncation mutant Δ28N+Δ791C has the following characteristics:

1. the optimum pH is 6.4, with a good pH tolerance between pH 5.8 and 8.0;
2. the optimum temperature for Δ28N+Δ791C is 100° C., and the remaining enzyme activity is greater than 60% after heat preservation at 100° C. for 2 h;
3. the specific enzyme activity of the mutant Δ28N+Δ791C is 32.18±0.92 U/mg, which is 5.99 times as high as that of the recombinant type II pullulanase Sumo-Pul$_{Py}$ (5.37±0.20 U/mg), thereby having important industrial application value and potential.

BRIEF DESCRIPTION OF FIGURES

in FIG. 2, 1 shows the low molecular weight protein Marker; 2 shows the cell lysate supernatant of BL21 (DE3)-pET-24a (+)-His+Sumo-Pul$_{Py}$; 3 shows the recombinant type II pullulanase Sumo-Pul$_{Py}$ purified by nickel column.

DETAILED DESCRIPTION (1) Strains and Vectors

The *E. coli* expression vector pET-24a(+) and the strain *Escherichia coli* BL21 (DE3) were purchased from Novagen.

(2) Enzymes and Other Biochemical Reagents

Restriction endonuclease, T4 DNA ligase, and PrimeSTAR MAX DNA polymerase were purchased from Takara Biomedical Technology (Beijing) Co., Ltd. Purification and plasmid extraction kits were purchased from Tiangen Biotech (Beijing) Co., Ltd. Pullulan was purchased from Shandong Freda Biotechnology Co., Ltd.; Amylose from potato and small molecule oligosaccharide standards were purchased from SIGMA-ALDRICH; Tryptone and Yeast Extract were purchased from UK OXOID (UK), and other reagents are domestic analytically pure.

(3) Medium

LB medium (g/L): yeast powder 5.0, Tryptone 10.0, NaCl 10.0, pH 7.0.

Plate-screening medium (g/L): Yeast powder 5.0, Tryptone 10.0, NaCl 10.0, agar 20.0, pH 7.0.

The molecular biology experiment methods that are not specifically explained in the following examples are all carried out with reference to the specific methods listed in J. Sambrock, *Molecular Cloning: A Laboratory Manual* (3rd edition), or according to kit and the instructions of product.

Example 1 Cloning and Recombinant Expression of Type II Pullulanase Gene

Figure 1:
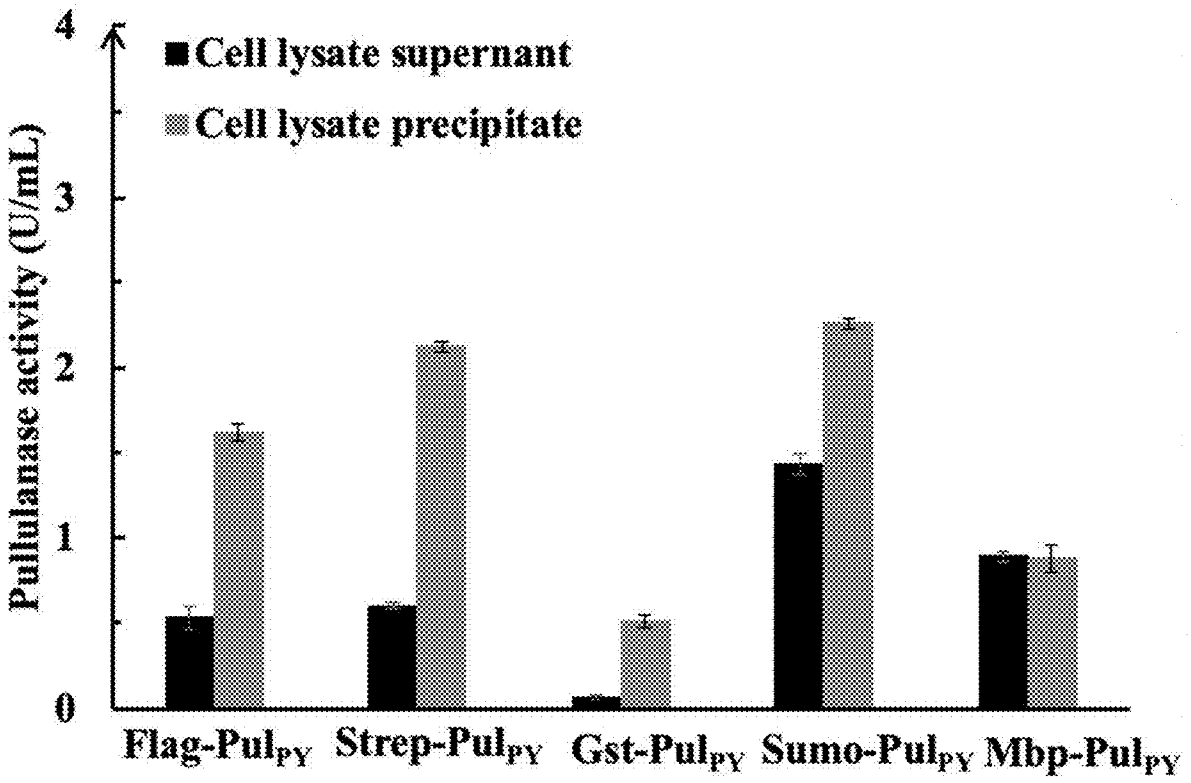
FIG. 1 shows the effect of different protein fusion tags on the expression of type II pullulanase Pul$_{Py}$.

The gene sequence was codon-optimized, according to the suspected type II pullulanase gene (The Genbank accession number: WP_013906427.1) derived from *Pyrococcus yayanosii* CH1, a deep-sea piezophilic hyperthermophilic archaeon. The optimized gene sequence (SEQ ID NO:2) was synthesized and connected to the restriction sites between BamH I and Xho I in the expression vector pET-24a(+) by General Biosystems (Anhui) Co., Ltd. to obtain a recombinant plasmid pET-24a(+)-Pul$_{Py}$. Next, the tag sequences Flag, Strep, Gst, Sumo, and Mbp were respectively synthesized to the restriction sites between Nde I and BamH I in pET-24a(+)-Pul$_{Py}$ by General Biosystems (Anhui) Co., Ltd. The T7 tags of the above recombinant plasmids were replaced and respectively transformed into *E. coli* BL21 (DE3), and the enzyme activity of recombinant type II pullulanase was compared. The results in FIG. 1 show that when Flag, Strep, Gst, Sumo, and Mbp tags are added, the intracellular enzyme activities of recombinant type II pullulanase are 2.15, 2.72, 0.58, 3.7, and 1.77 U/mL, respectively. It can be seen that the Sumo tag has a better effect on the expression of recombinant type II pullulanase.

In order to obtain the pure protein of recombinant type II pullulanase Sumo-Pul$_{Py}$, a nucleic acid sequence containing both His and Sumo tags was synthesized by General Biosystems (Anhui) Co., Ltd. and connected to the restriction sites between Nde I and BamH I in pET-24a(+)-Pul$_{Py}$ to obtain pET-24a(+)-His+Sumo-Pul$_{Py}$ which was transformed into *E. coli* BL21 (DE3).

Figure 2:
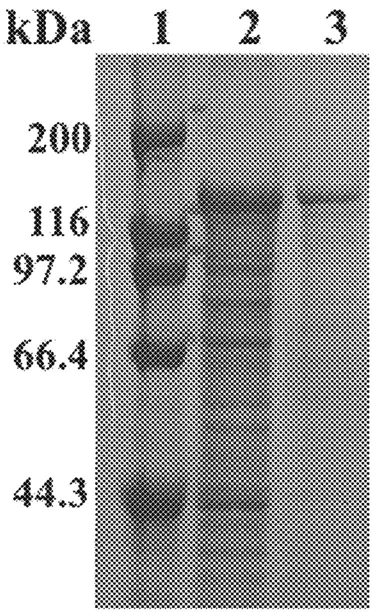
FIG. 2 shows the SDS-PAGE diagram of recombinant type II pullulanase Sumo-Pul$_{Py}$ expressed in *E. coli*.

BL21 (DE3)-pET-24a(+)-His+Sumo-Pul$_{Py}$ was inoculated into 5 mL of LB culture medium (50 μg/mL kanamycin), and cultured overnight at 37° C. The cultured bacterial solution was inoculated into 50 mL of LB culture medium (added with 50 μg/mL kanamycin) with an inoculum of 1% and cultured with shaking at 37° C. for about 2 to 3 h. After $OD_{600}$ reaching 0.6, an inducer IPTG was added with a final concentration of 2 mmol/L, the mixture was cultured with shaking at 220 rpm at 16° C. for 16 h and centrifuged at 12000 rpm for 5 min, and the supernatant of medium was collected. DNS method was used to determine the activity of recombinant type II pullulanase Sumo-Pul$_{Py}$. The SDS-PAGE results in FIG. 2 show that the recombinant type II pullulanase Sumo-Pul$_{Py}$ was expressed in *E. coli*, and the protein content of the expressed recombinant type II pullulanase Sumo-Pul$_{Py}$ reaches more than 90% of the total protein after affinity purification through a nickel column.

Example 2 Determination of Properties of Recombinant Type II Pullulanase Sumo-Pul$_{Py}$ 1. Determination of the Activity of the Recombinant Type II Pullulanase Sumo-Pul$_{Py}$ The determination of the activity of recombinant type II pullulanase Sumo-Pul$_{Py}$ was adopted the 3,5-dinitrosalicylic acid (DNS) method. The specific steps were as follows: reacting 100 μL reaction system (10 μL potassium phosphate buffer with different pH with a final concentration of 100 mM, 50 μL pullulan with a final concentration of 3% and 40 μL enzyme solution) at a certain temperature for 15 min, adding 100 μL DNS reaction solution, boiling in a water bath for 6 min, immediately cooling to room temperature with running water, adding and diluting with distilled water, mixing well, and determining $OD_{476}$. One enzyme activity unit (U) was defined as the amount of enzyme required to release reducing sugar correspond to the reduction capacity of 1 μmol glucose per minute under assay conditions.

2. Determination of the Optimum pH and pH Stability of the Recombinant Type II Pullulanase Sumo-$Pul_{Py}$ Determination of the optimum pH: the purified Sumo-$Pul_{Py}$ was subjected to enzymatic reaction in 100 mM potassium phosphate buffer (pH 5.8-8.0) at 95° C.

Figure 3:
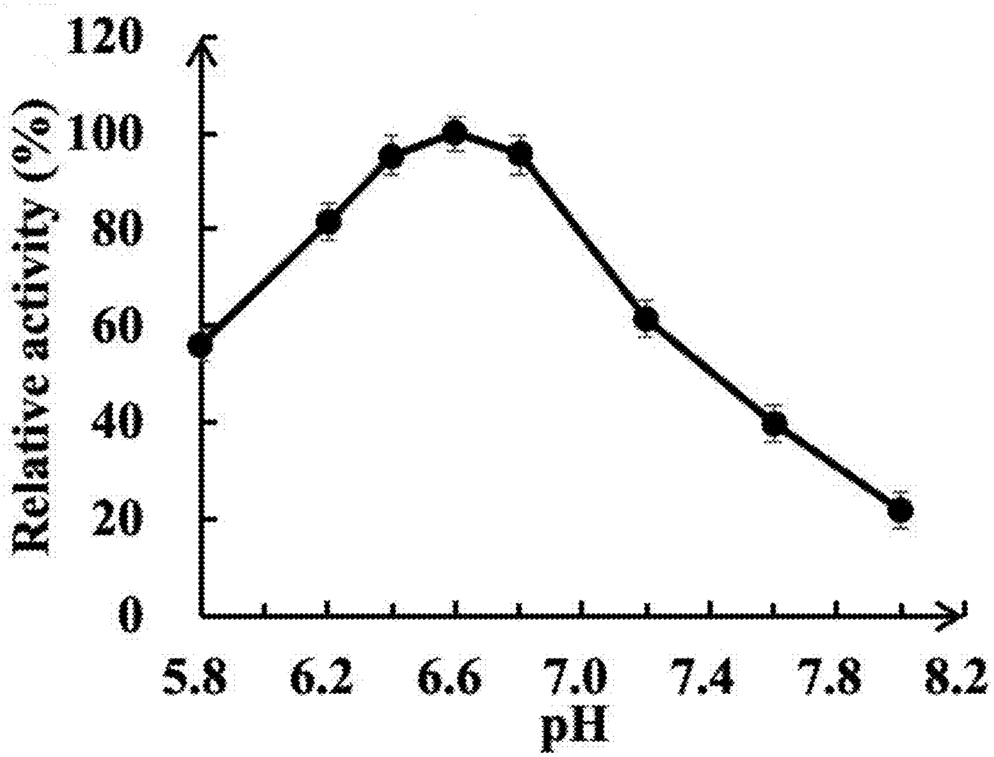
FIG. 3 shows the relative enzyme activity of recombinant type II pullulanase Sumo-Pul$_{Py}$ under different pH conditions.
Figure 4:
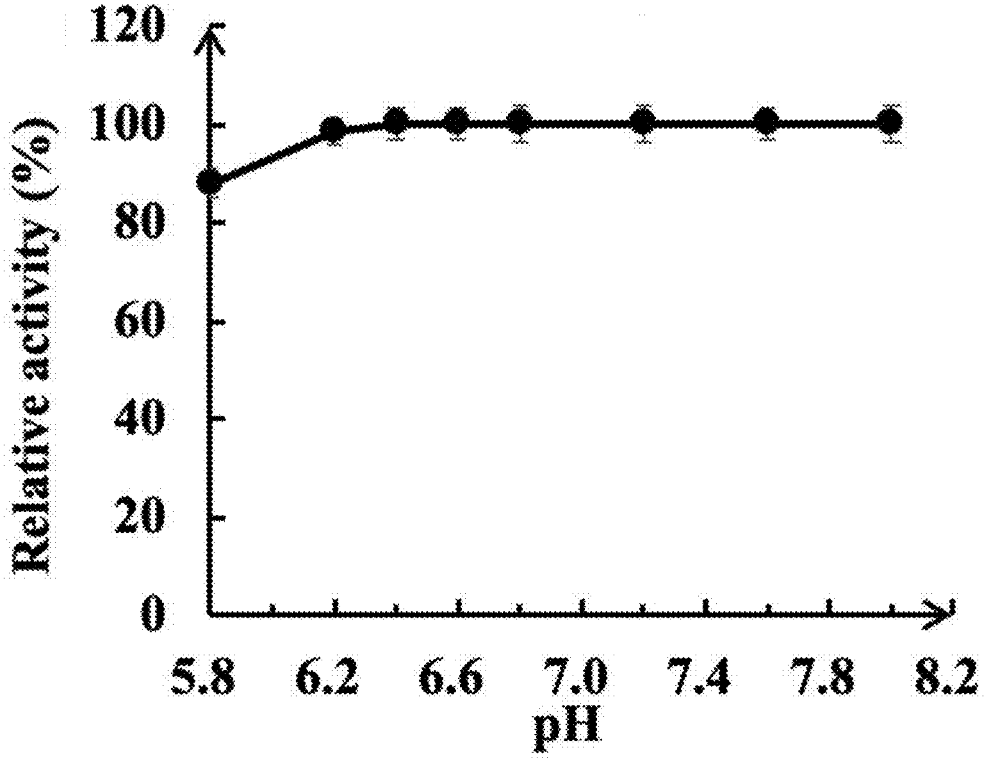
FIG. 4 shows the pH stability of recombinant type II pullulanase Sumo-Pul$_{Py}$.

Determination of the pH stability of the enzyme: the enzyme solution was added into 100 mM potassium phosphate buffer (pH 5.8-8.0) and disposed at 4° C. for 4 h, and then the enzymatic reaction was performed at pH 6.6 and 95° C. to determine the remaining enzyme activity of Sumo-$Pul_{Py}$. The results show that the optimum pH of Sumo-$Pul_{Py}$ is 6.6 (FIG. 3); Sumo-$Pul_{Py}$ is very stable between pH 5.8 and 8.0. Except for a 12% loss of enzyme activity after disposal at pH 5.8 for 4 h, the rest has almost no effect on the enzyme activity (FIG. 4).

3. Optimum Temperature and Thermal Stability of Recombinant Type II Pullulanase Sumo-$Pul_{Py}$ Determination of the optimum temperature of the enzyme: the enzymatic reaction was performed in a potassium phosphate buffer (pH 6.6) at 75-100° C.

Figure 5:
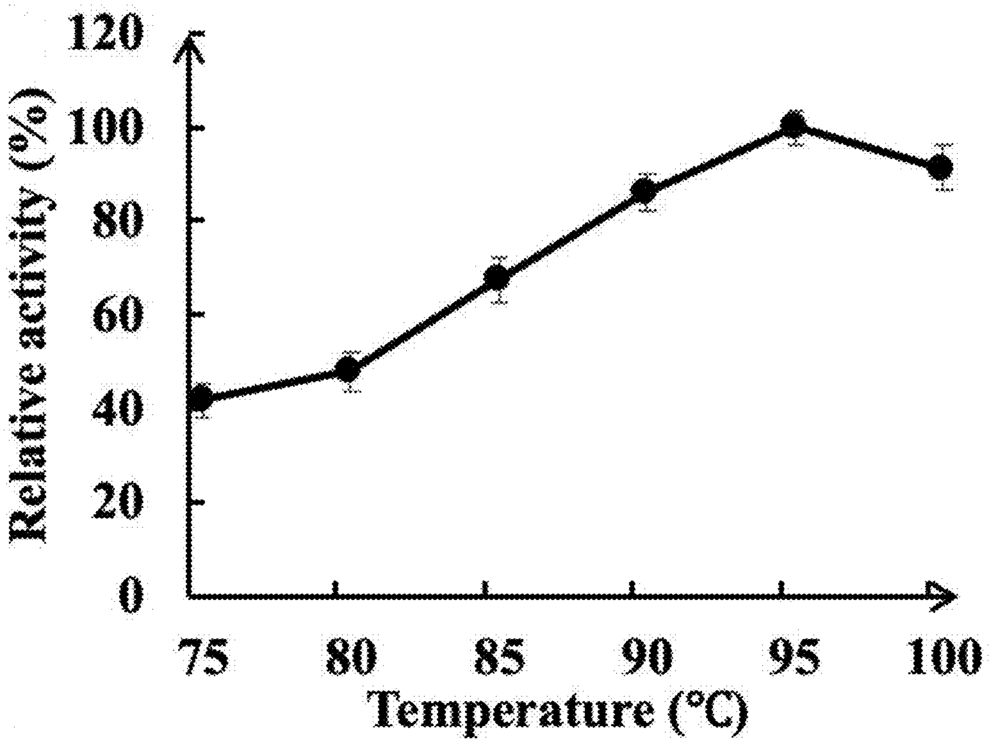
FIG. 5 shows the relative enzyme activity of recombinant type II pullulanase Sumo-Pul$_{Py}$ under different temperature conditions.
Figure 6:
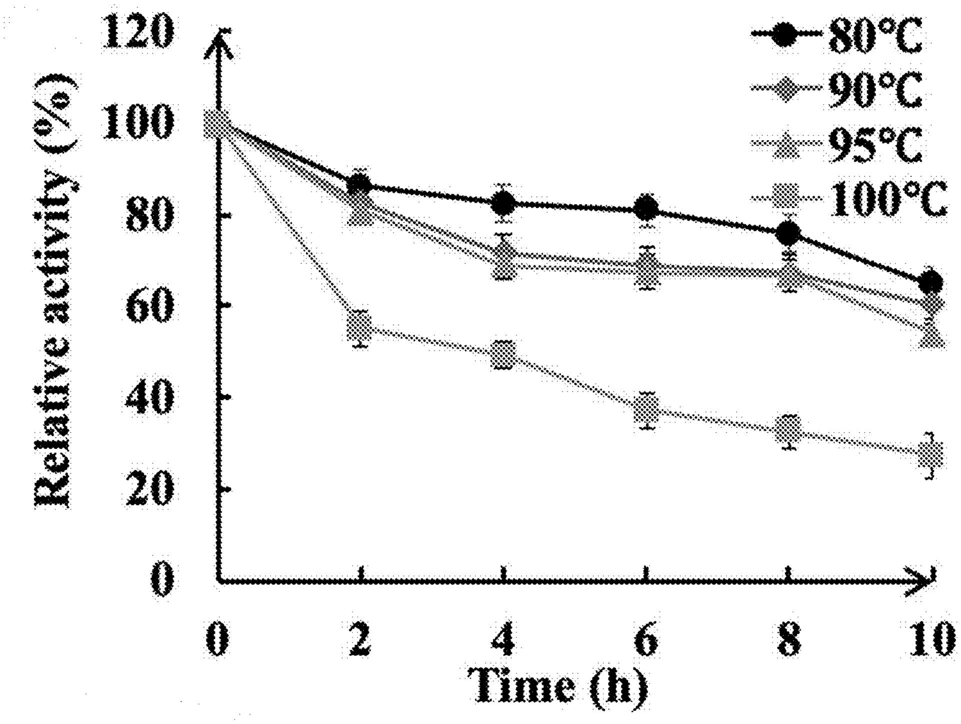
FIG. 6 shows the thermal stability of recombinant type II pullulanase Sumo-Pul$_{Py}$.

Determination of the thermal stability of the enzyme: the enzyme solution with the same amount of enzyme was placed under the conditions of 80° C., 90° C., 95° C. and 100° C., respectively, and disposed for 2 h, 4 h, 6 h, 8 h and 10 h, respectively, and the enzymatic reaction was performed at pH 6.6 and 95° C. to determine the remaining enzyme activity of Sumo-$Pul_{Py}$. The determination results of the optimum temperature for the enzyme reaction in FIG. 5 show that the optimum temperature is 95° C. The determination results of the thermal stability of enzyme in FIG. 6 show that the remaining enzyme activity is greater than 50% after Sumo-$Pul_{Py}$ heat preservating at 95° C. for 10 h, which indicates that the enzyme has good thermal stability.

4. Kinetic Parameters of the Recombinant Type II Pullulanase Sumo-$Pul_{Py}$

Using different concentrations of pullulan (1.25, 2.5, 5, 10, 20, and 40 mg/mL) as the substrate, the enzyme activity was determined under the optimum conditions, the corresponding reaction rate was calculated, and Km value and Vmax were obtained by Linewear Burk method using Michaelis-Menten Equation. The results show that the Vmax of the enzyme is 5.37±0.20 U/mg, and the Km is 8.78±0.89 mg/mL.

5. Effect on Different Metal Ions and Chemical Reagents on the Enzyme Activity of Recombinant Type II Pullulanase Sumo-$Pul_{Py}$ 2 mM metal ions and a certain concentration of chemical reagents were added to the enzymatic reaction system to investigate their effects on Sumo-$Pul_{Py}$ activity. When metal ions and chemical reagents were not added, Sumo-$Pul_{Py}$ had a specific enzyme activity of 5.37±0.20 U/mg under the condition of 95° C. and pH 6.6, and the relative enzyme activity was 100% at this time. The results in Table 1 show that $Fe^{2+}$, $Co^{2+}$, DTT, and β-mercaptoethanol can increase the activity of Sumo-$Pul_{Py}$ by higher than 40%, and the addition of DTT can increase the activity of Sumo-$Pul_{Py}$ by 237.2%; $K^+$, Triton X-100, and Tween-80 weakly promote the enzyme activity of Sumo-$Pul_{Py}$; other reagents inhibit the activity of Sumo-$Pul_{Py}$ to a certain extent.

TABLE 1

Effects on metal ions and chemical reagents on the activity of Sumo-$Pul_{Py}$

| Reagent | Concentration | Relative enzyme activity (%) |
|---|---|---|
| None | — | 100 ± 2.8 |
| $CaCl_2$ | 2 mM | 71.3 ± 3.5 |
| $MnCl_2$ | 2 mM | 91.2 ± 2.9 |
| $FeSO_4$ | 2 mM | 183.1 ± 4.0 |
| $NiSO_4$ | 2 mM | 73.3 ± 3.3 |
| $CoCl_2$ | 2 mM | 150.0 ± 4.8 |
| $CuCl_2$ | 2 mM | 45.9 ± 3.5 |
| $MgCl_2$ | 2 mM | 94.9 ± 3.4 |
| NaCl | 2 mM | 81.1 ± 4.2 |
| $ZnSO_4$ | 2 mM | 0 |
| KCl | 2 mM | 104.1 ± 3.0 |
| DTT | 1% | 337.2 ± 4.7 |
| Triton X-100 | 1% | 111.1 ± 3.6 |
| β-mercaptoethanol | 1% | 157.4 ± 3.0 |
| Tween-80 | 1% | 110.8 ± 2.9 |

6. Analysis of the Degradation Products of Pullulan and Amylose by Recombinant Type II Pullulanase Sumo-$Pul_{Py}$ The sample processing procedure was as follows: an appropriate amount of pure enzyme solution was mixed well with 1% pullulan and 1% Amylose from potato respectively, enzymatically hydrolyzed at 95° C. for 6 h, cooled to room temperature and then centrifuged at 12000 r/min for 20 min. And the supernatant was taken. The enzymatic hydrolysis products of pullulan and Amylose from potato were analyzed using high performance liquid chromatography (HPLC, conditions: Hpersil $NH_2$ amino column (4.6×250 mm), column temperature 40° C., mobile phase (acetonitrile:water=67:33), flow rate 1.0 mL/min, injection volume 20 μL) and MALDI-TOF/TOF matrix-assisted laser analysis/ionization tandem time-of-flight mass spectrometer respectively.

Figure 7:
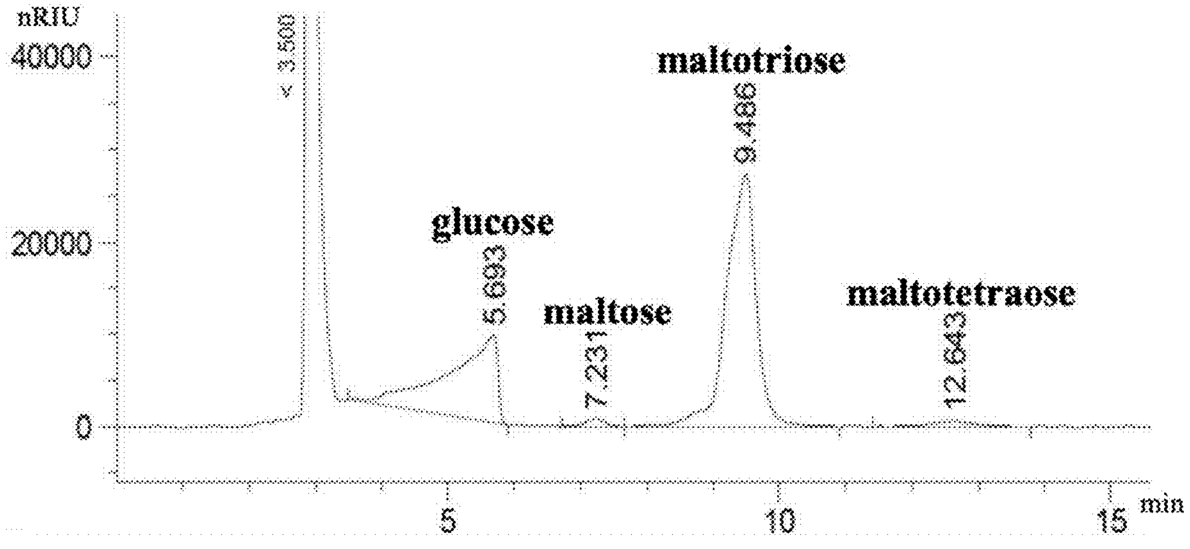
FIG. 7 shows the degradation products of pullulan by recombinant type II pullulanase Sumo-Pul$_{Py}$.
Figure 8:
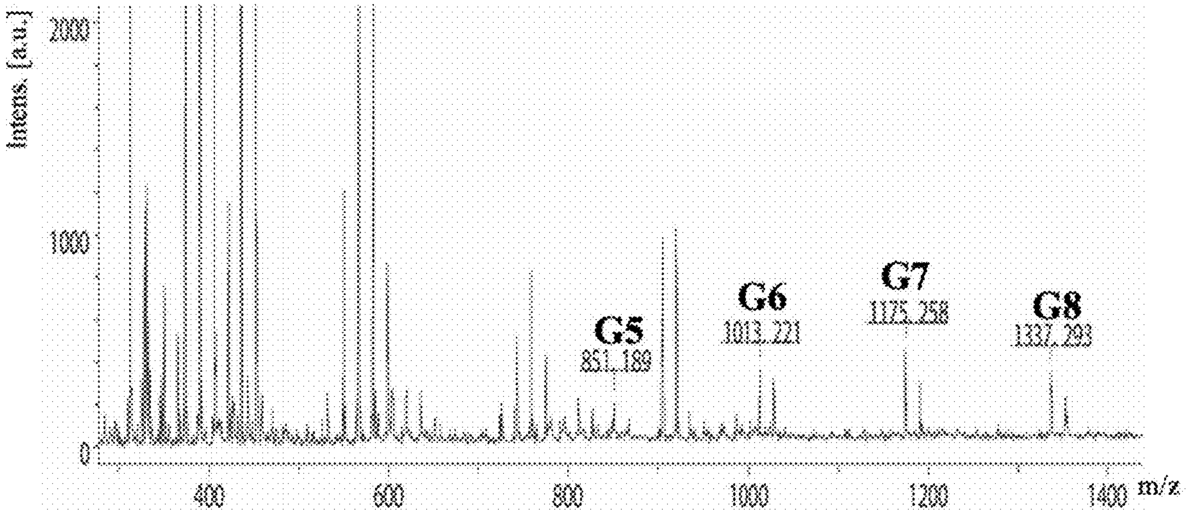
FIG. 8 shows the degradation products of Amylose from potato by recombinant type II pullulanase Sumo-Pul$_{Py}$.

The results show that most of the pullulan hydrolysates are maltotriose, and there is no panose and isopanose in the hydrolysate, which indicates that Sumo-$Pul_{Py}$ has a specific hydrolysis effect on the α-1,6-glycosidic linkage in pullulan, and belongs to pullulanase (FIG. 7); the hydrolysate of Amylose from potato by Sumo-$Pul_{Py}$ are mainly oligosaccharides such as pentasaccharides, hexasaccharides, heptasaccharides, and octasaccharides, which indicates that the enzyme also has a certain hydrolysis capacity on the α-1, 4-glycosidic linkage in Amylose from potato and has the function of α-amylase (FIG. 8). In summary, Sumo-$Pul_{Py}$ belongs to type II pullulanase.

Figure 9:
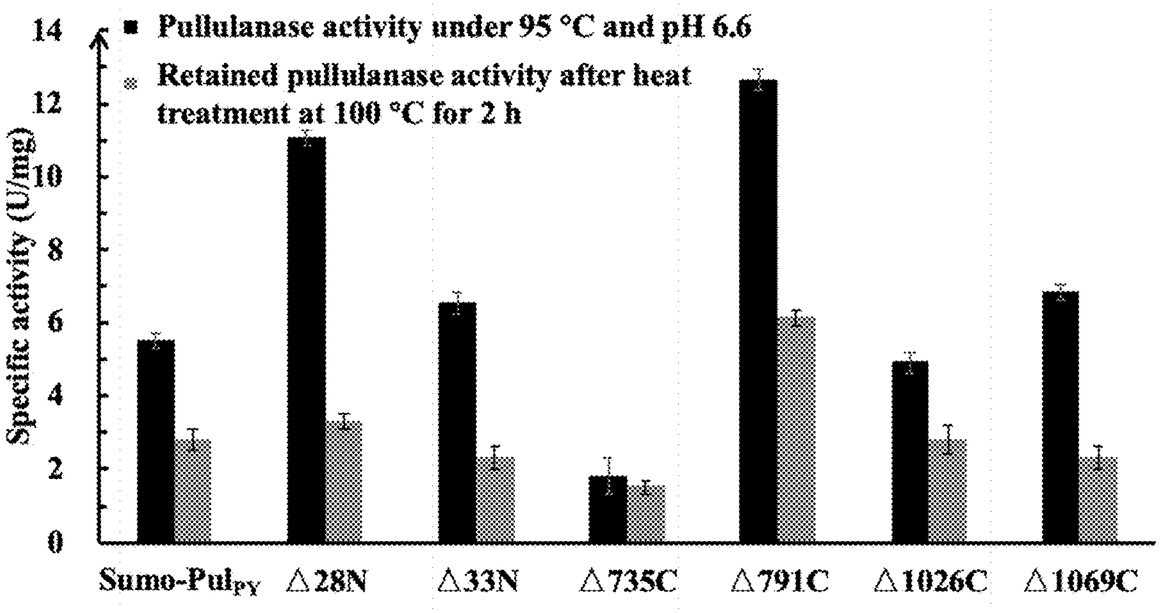
FIG. 9 shows the remaining specific enzyme activity of truncation mutant of Sumo-Pul$_{Py}$ after heat preservation at 95° C. and 100° C. for 2 h.

Example 3 Analysis of the Enzymatic Properties of the Truncation Mutant Δ28N+Δ791C of Type II Pullulanase Sumo-$Pul_{Py}$ First, the first 28 and 33 amino acids at the N-terminal of Sumo-$Pul_{Py}$ were deleted and the amino acids after positions 734, 784, 790, 1021, 1025, 1068, and 1077 at the C-terminal of Sumo-$Pul_{Py}$ were deleted respectively. The obtained 9 $Pul_{Py}$ truncated gene sequences were respectively synthesized and connected to the restriction sites between BamH I and Xho I in the vector pET-24a(+)-His+Sumo-$Pul_{Py}$ by General Biosystems (Anhui) Co., Ltd. The obtained 9 new recombinant plasmids were transformed into *E. coli* BL21 (DE3) respectively. The results show that the specific enzyme activity of Δ735C at 95° C. is 0.33 time as high as that of Sumo-$Pul_{Py}$, and the remaining specific enzyme activity after heat preservation at 100° C. for 2 h is 1.5 U/mg, while the specific enzyme activity of Δ28N and Δ791C at 95° C. are 2.02 and 2.31 times as high as that of Sumo-Pul$_{Py}$ respectively, and the remaining specific enzyme activity of the two after heat preservation at 100° C. for 2 h are also increased to a certain extent compared with Sumo-Pul$_{Py}$ (FIG. 9).

Figure 10:
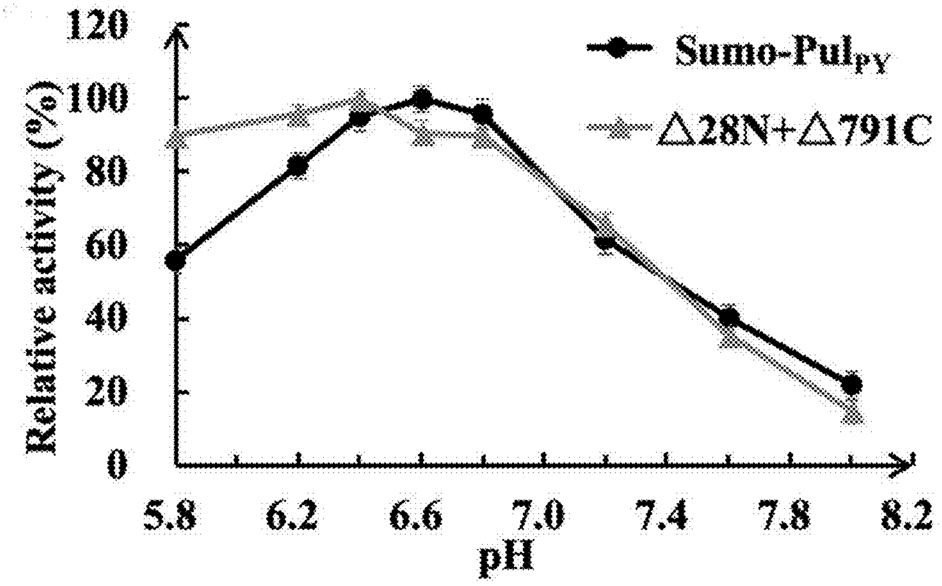
FIG. 10 shows the relative enzyme activity of the combined truncation mutant Δ28N+Δ791C under different pH conditions.
Figure 11:
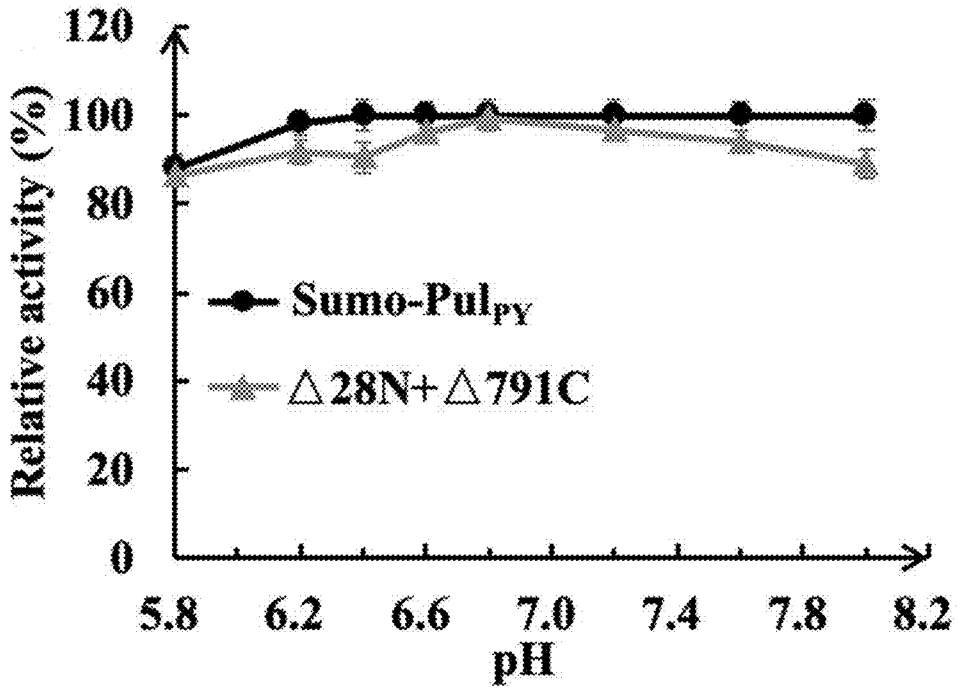
FIG. 11 shows the pH stability analysis of the combined truncation mutant Δ28N+Δ791C.
Figure 12:
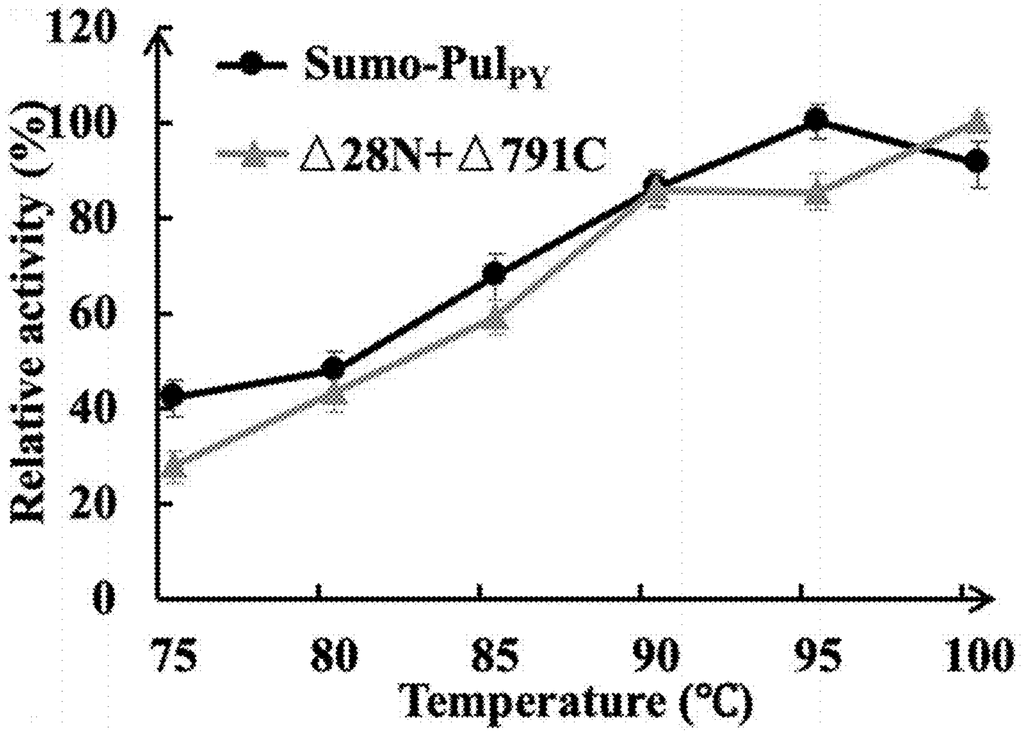
FIG. 12 shows the relative enzyme activity of the combined truncation mutant Δ28N+Δ791C under different temperature conditions.
Figure 13:
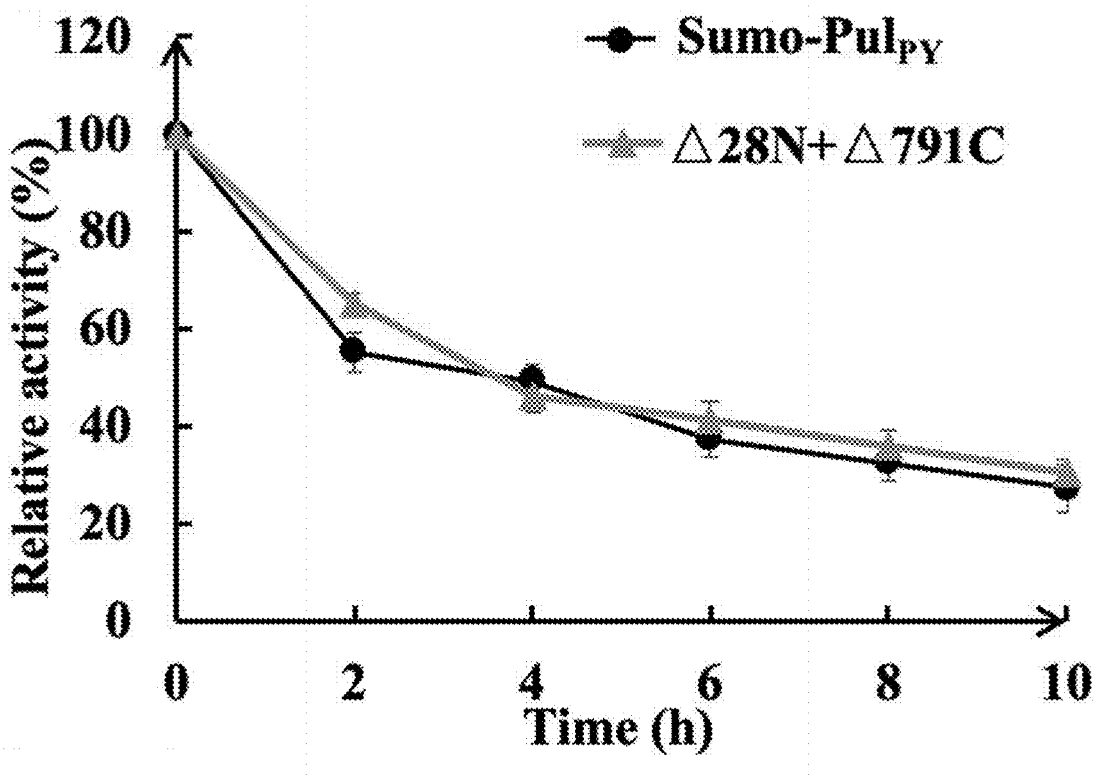
FIG. 13 shows the thermal stability of the combined truncation mutant Δ28N+Δ791C under the condition of 100° C.

Afterwards, the first 28 amino acids at the N-terminal of Pul$_{Py}$ and the amino acids after position 790 at the C-terminal of Pul$_{Py}$ were deleted to obtain the combined truncation mutant Δ28N+Δ791C (the amino acid sequence is set forth in SEQ ID NO:3). The expression and purification conditions and the analysis method of enzymatic properties for Δ28N+Δ791C were the same as those of Sumo-Pul$_{Py}$. The results show that the optimum pH of Δ28N+Δ791C is 6.4, which has a clear tendency to shift to acidity compared with Sumo-Pul$_{Py}$ (FIG. 10); Δ28N+Δ791C has good pH tolerance between pH 5.8 and 8.0 (FIG. 11); the optimum temperature of Δ28N+Δ791C is 100° C., which improves 5° C. compared with that of Sumo-Pul$_{Py}$ (FIG. 12); the thermal stability of Δ28N+Δ791C at 100° C. slightly improves compared with that of Sumo-Pul$_{Py}$ (FIG. 13). In terms of kinetic parameters, the Vmax of Δ28N+Δ791C is 32.18±0.92 U/mg, and the specific enzyme activity is 5.99 times as high as that of Sumo-Pul$_{Py}$ (5.37±0.20 U/mg); Km is 6.63±0.56 mg/mL, which is slightly reduced compared with that of Sumo-Pul$_{Py}$ (8.78±0.89 mg/mL), indicating that the affinity of Δ28N+Δ791C to the substrate has been improved to a certain extent.

Comparative Example

The suspected type II pullulanase gene (The Genbank accession number: WP_013906427.1) derived from *Pyrococcus yayanosii* CH1, a deep-sea piezophilic hyperthermophilic archaeon, was synthesized, and the gene was connected to the restriction sites between BamH I and Xho I in the expression vector pET-24a(+) to obtain a recombinant plasmid pET-24a(+)-Pul$_{Py}$. The recombinant plasmid was transformed into *E. coli* BL21 (DE3). According to the culture method of Example 1, the expression of type II pullulanase gene was not detected.

Although the present disclosure has been disclosed in the above preferred examples, it is not intended to limit the present disclosure. Any person familiar with the technology can make various modifications and changes without departing from the spirit and scope of the present disclosure. Therefore, the protection scope of the present disclosure should be defined by the claims.

What is claimed is:

1. A recombinant *Escherichia coli*, wherein the recombinant *E. coli* expresses a type II pullulanase that has 100% sequence identity to SEQ ID NO:3, and wherein the type II pullulanase is encoded by a nucleotide sequence that has 100% sequence identity to SEQ ID NO:4, wherein the type II pullulanase is from *Pyrococcus* yayanosii CH1, and wherein SEQ ID NO:3 comprises a double truncation mutation at Δ28N and Δ791C as compared with a wild type *Pyrococcus* yayanosii CH1 type II pullulanase peptide sequence.

2. The recombinant *E. coli* according to claim 1, wherein the type II pullulanase is encoded on a pET series vector.

3. The recombinant *E. coli* according to claim 2, wherein the pET series vector is a pET-24a(+) vector.

4. The recombinant *E. coli* according to claim 1, wherein the *E. coli* is an BL21 (DE3) *E. coli* strain.

5. The recombinant *E. coli* according to claim 1, wherein the type II pullulanase possesses an optimum enzyme activity at a pH of 6.4, and wherein the type II pullulanase possesses enzyme activity in a pH range of from 5.8 to 8.0.

6. The recombinant *E. coli* according to claim 1, wherein the type II pullulanase possesses an optimal enzyme activity at 100° C., and wherein the type II pullulanase enzyme remains at least 60% active after incubation for 2 hours at 100° C.

7. The recombinant *E. coli* according to claim 1, wherein a specific activity of the type II pullulanase is increased by 5.99 times as compared to the specific activity of the wild type II pullulanase.

8. A method of preparation of the recombinant *E. coli* of claim 1, wherein the method comprises:

providing the nucleotide sequence of the type II pullulanase encoded by SEQ ID NO: 4;

ligating the nucleotide sequence of the type II pullulanase to an expression vector to obtain a recombinant plasmid; and, transforming the recombinant plasmid into a BL21 (DE3) *E. coli* strain.

9. A method of producing the type II pullulanase of claim 3, which comprises contacting a fermentation medium with the recombinant *E. coli* under conditions that induce expression of the type II pullulanase from the recombinant *E. coli*.

10. The method according to claim 9, further comprising:

inoculating a cultured seed solution of recombinant *E. coli* into Luria broth (LB) medium with an inoculum of 1% to 5%, incubating the medium with shaking at 35° C. to 38° C. until an $OD_{600}$ measurement reaches 0.4 to 0.6, adding IPTG at a final concentration of 1 mmol/L to 2 mmol/L to the medium, and continuing incubating with shaking at 15° C. to 16° C. for 15 hours to 20 hours.

11. The method according to claim 10, wherein the seed solution of recombinant *E. coli* is obtained by inoculating the recombinant *E. coli* into the medium and incubating at 35° C. to 38° C. for 10 hours to 14 hours.

* * * * *